United States Patent [19]
Timmermans

[11] Patent Number: 5,961,478
[45] Date of Patent: Oct. 5, 1999

[54] SUPER ABSORBENT WOUND DRESSING

[75] Inventor: Claus J. Timmermans, Havelte, Netherlands

[73] Assignee: AM International Tesla AG, Havelte, Netherlands

[21] Appl. No.: 09/059,463

[22] Filed: Apr. 14, 1998

[30] Foreign Application Priority Data

Apr. 15, 1997 [NL] Netherlands .................... 1005812

[51] Int. Cl.⁶ .................................................. A61F 13/00
[52] U.S. Cl. .............................................. 602/41; 602/56
[58] Field of Search ........................................ 602/41, 56

[56] References Cited

U.S. PATENT DOCUMENTS 5,002,814   3/1991   Knack, et al. ......................... 428/85

*Primary Examiner*—John G. Weiss
*Assistant Examiner*—Kelvin Hart
*Attorney, Agent, or Firm*—Stevens, Davis, Miller & Mosher, L.L.P.

[57] ABSTRACT

This invention relates to wound dressings with the ability to absorb large amounts of wound fluids and water. For this purpose a super absorbent fiber is used, preferably consisting of polyacrylnitrile. The absorptive power of this fiber is obtained by saponification of surface molecules of the fiber. Through this, the core of the fiber will remain inviolable and the stability of the fiber is ensured. Therefore, wound dressings with super absorbent qualities can be easily produced.

6 Claims, No Drawings

SUPER ABSORBENT WOUND DRESSING

This invention relates to wound dressing which is constructed using a super absorbent insoluble or not degrading fibre. Wound dressing serve to protect the wound against external influences, to absorb wound fluids or to keep the wound moisturised when used as wet dressings. At the same time bacterial growth in the wound must be prevented. Not all these requirements can be made using a traditional cotton gauze dressing. Hydrogels and hydrocolloides with a polyurethane matrix as a base proved to be better suitable in relation to absorbing fluids than cotton gauze dressings. The absorbing capacity however is limited and therefore often not sufficient also. Moreover these dressings do not breathe well and are not suitable for use as wet dressings.

To improve the fluid absorbtion and the fluid binding in hygiene products P. acid salts are used. These can bind up to 80 times there own weight in water because of "van der Waals forces". Salts of polyacrylic acid, available as powder, made up of fine crystals or little granules can be added to wound dressing materials. The powder with water will form a gel. This gel may not get into the wound or be left in the wound. Therefore the preparation of a wound dressing with polyacrylic acid is usually complex and costly. For instance the fluid absorptive powder can be glued onto a membrane of cellulose. This membrane will than have to be enclosed by a finely woven material.

By chance it is proven that the structure of polyacrylnitrile fibres is changed when led through saponifying baths. The fibre then shows a polyacrylnitrile core enclosed by a coating of polyacrylic acid or salts of polyacrylic acid. In addition it is proven by chance, that by using these fibres wound dressing with a super-absorbing nature can be produced easily. These wound dressing materials can absorb up to 60 times their weight in water. The fibres will swell but will remain intact because of the core of the fibres.

For example

Celwool fibres and super absorbent fibres can be worked into a "non woven" membrane in proportion of 30 to 70. This membrane will be coated with a thin layer of celwool fibres and polyacrylnitrile fibres on both sides. On one or both sides of the wound dressing a mesh of HD polyethylene is applied.

I claim:

1. A wound dressing comprising a super absorbent fiber being able to bind extremely large amount of water or other fluids without showing any tendency to disintegrate into a gel like structure, said super absorbent fibers comprising a core of polyacrylnitrile and a coating of acrylic acid-or acrylic acid salts on said core.

2. The wound dressing of claim 1 further comprising, in combination with said super absorbent fibers, at least one fiber selected from the group consisting of celwool and cotton.

3. The wound dressing of claim 1 further comprising a non-woven membrane into which the super absorbent fibers are worked.

4. The wound dressing of claim 3 in which said membrane is coated with a thin layer of said fibers on both sides.

5. The wound dressing of claim 4 further comprising a mesh of high density polyethylene on at least one side of said wound dressing.

6. The wound dressing of claim 1, wherein said coatings are applied by leading said polyacrylnitrile fibers through saponification baths.

* * * * *